US009895106B1

(12) United States Patent
Graybill et al.

(10) Patent No.: US 9,895,106 B1
(45) Date of Patent: *Feb. 20, 2018

(54) HAND-MOUNTED NETWORKED IMAGING DEVICES

(71) Applicant: Amazon Technologies, Inc., Seattle, WA (US)

(72) Inventors: Jules Cook Graybill, Seattle, WA (US); James Christopher Curlander, Mercer Island, WA (US); Danny Guan, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 193 days.

This patent is subject to a terminal disclaimer.

(21) Appl. No.: 14/500,521

(22) Filed: Sep. 29, 2014

(51) Int. Cl.
*G06K 7/10* (2006.01)
*A61B 5/00* (2006.01)
*A61B 1/06* (2006.01)

(52) U.S. Cl.
CPC .............. *A61B 5/6806* (2013.01); *A61B 1/06* (2013.01); *A61B 5/0082* (2013.01); *A61B 5/6825* (2013.01); *A61B 5/742* (2013.01)

(58) Field of Classification Search
CPC ................. G06K 7/10881; G06K 7/10891

USPC ....................... 235/472.01, 462.45
See application file for complete search history.

(56) References Cited

U.S. PATENT DOCUMENTS

| 6,151,208 | A | * | 11/2000 | Bartlett | G06F 1/1626 361/679.03 |
| 8,009,141 | B1 | * | 8/2011 | Chi | G06F 3/0317 345/156 |
| 9,235,742 | B1 | * | 1/2016 | Qaddoura | G06T 3/60 |
| 2006/0108425 | A1 | * | 5/2006 | Wiklof | 235/462.44 |
| 2014/0249944 | A1 | * | 9/2014 | Hicks et al. | 705/17 |

* cited by examiner

*Primary Examiner* — Daniel St Cyr
(74) *Attorney, Agent, or Firm* — Athorus, PLLC

(57) ABSTRACT

Imaging devices may be mounted to one or more hands of a worker, e.g., on a glove or other substrate that maybe worn on the hands of the worker, and used to capture images or imaging data from a perspective associated with the hands. The images or imaging data may be stored, analyzed or displayed on a computer display, e.g., a display provided on the glove or substrate. Additionally, the images or imaging data may be evaluated to determine whether a task has been properly performed by the worker, such as by identifying one or more markings (e.g., bar codes) that may be provided within the images or the imaging data.

5 Claims, 10 Drawing Sheets

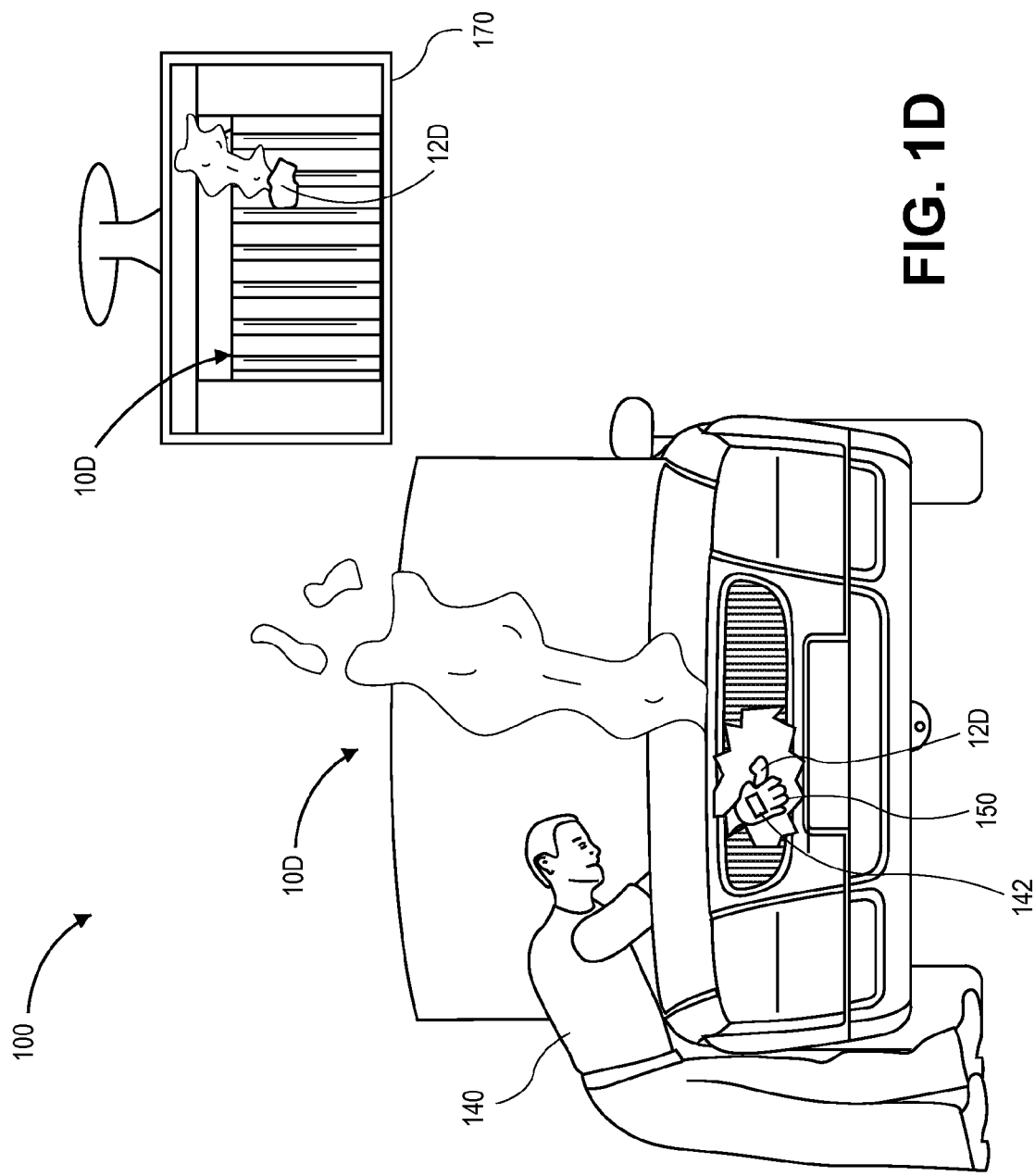

HAND-MOUNTED NETWORKED IMAGING DEVICES

BACKGROUND

Naturally, humans see with their eyes and work with their hands. Indeed, human bodies are equipped with a pair of eyes that are provided on their faces and pointed in a forward direction. The eyes are configured to receive light from direct or reflected sources, and to transmit signals regarding the received light to the brain, where such signals may be processed and associated with one or more still or moving images. Likewise, a human body is also bestowed with a pair of hands, each of which is provided on distal ends of arms that are mounted to a torso by a pair of shoulders, and the motor cortex of the brain may control the coarse or fine movements of the arms, the wrists, the hands or fingers. Therefore, by virtue of immutable aspects of their physiological construction, humans have organs for visually sensing conditions of an environment in which they are situated, viz., their eyes, that are provided approximately two to three feet, on average, from organs for performing one or more tasks, viz., hands. The distance between such organs is usually defined as a function of an individual human's arm and/or neck length.

Occasionally, humans must perform tasks on a subject using their hands in situations in which a clear line of sight between the eyes and the subject is unavailable or at least partially obscured. For example, a human may be required to reach into a cluttered toolbox in order to retrieve a small tool, or into murky pond waters in order to search for a lost jewelry item. Similarly, humans may also perform tasks on small materials or items, or within confined spaces. In such situations, the distance between the human's eyes and the human's hands may act as a functional impediment to the proper performance of such tasks.

Computer systems are commonly used to register or otherwise acknowledge the presence, transfer or arrival of an item, an object, a person or a thing using one or more scanners or readers, which may be configured to acknowledge or optically recognize text, numbers or other identifiers (e.g., a one-dimensional bar code or a two-dimensional quick response bar code, or "QR" bar code) that may be printed, written, affixed, marked or otherwise associated with an item, an object, a person or a thing. Such scanners or readers may be used in any number of environments or facilities such as airports, shopping malls or warehouses, where such scanners or readers may optically scan, read or otherwise evaluate an airline ticket, an item for purchase, or a shipment of items that has arrived or is scheduled to depart.

Originally associated with large, fixed consoles or machines, scanners or readers are now typically associated with handheld computing devices or other grippable machines. After obtaining an item, holding or gripping the item in one hand, and locating an identifier affixed or labeled thereon, a worker may scan or read the identifier with the handheld scanner or reader. Although the use of a handheld scanner or reader may efficiently register or acknowledge the presence, transfer or arrival of items, objects, people or things, the actual use of such systems or devices may result in some unexpected or undesired circumstances. For example, a worker's manual use of a handheld scanner or reader to identify items typically requires the worker to stop his or her motion, to place an item in a field of view of the scanner or reader with one hand and to command the scanner or reader to capture an image of a portion of the item with another hand. The break in motion, and the described events, must be repeated for each and every instance in which an item is to be recognized.

BRIEF DESCRIPTION OF THE DRAWINGS

FIGS. 1A, 1B, 1C and 1D are views of hand-mounted networked imaging devices, in accordance with embodiments of the present disclosure.

DETAILED DESCRIPTION

As is set forth in greater detail below, the present disclosure is directed to imaging systems that may be worn or otherwise provided on one or more hands of a user, e.g., within one or more gloves or like articles of apparel, and used to capture any type or form of imaging data from a perspective of the hands. The imaging systems may include one or more imaging devices, such as digital cameras or other sensors, and any associated accessories, including but not limited to illuminators, flashes or other light sources for projecting light within a vicinity of the imaging systems; microphones for capturing audible signals or sounds; monitors or other display devices for playing audio or video files; as well as one or more computer processors, data stores, network interfaces or other computer components. Additionally, the imaging data captured by imaging systems in accordance with the present disclosure may be used to determine information regarding conditions in an environment in a vicinity of the hand, e.g., by displaying or recording and subsequently analyzing still or moving images or other multimedia captured using such systems, or to identify one or more objects within the environment, e.g., by recognizing and/or interpreting one or more aspects of such images, including but not limited to bar codes, markings or other identifiers expressed therein.

Figure 1A:
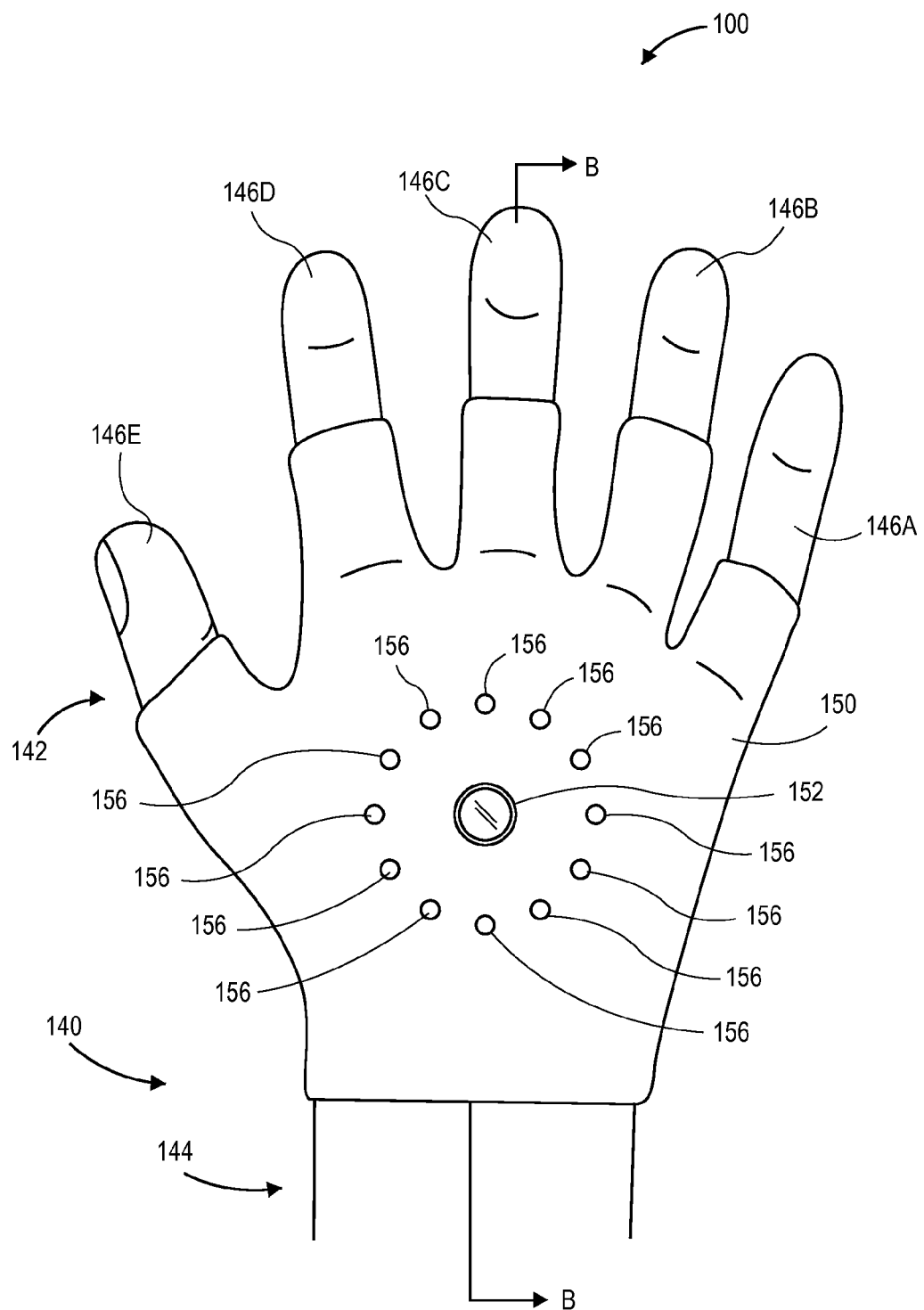
Figure 1B:
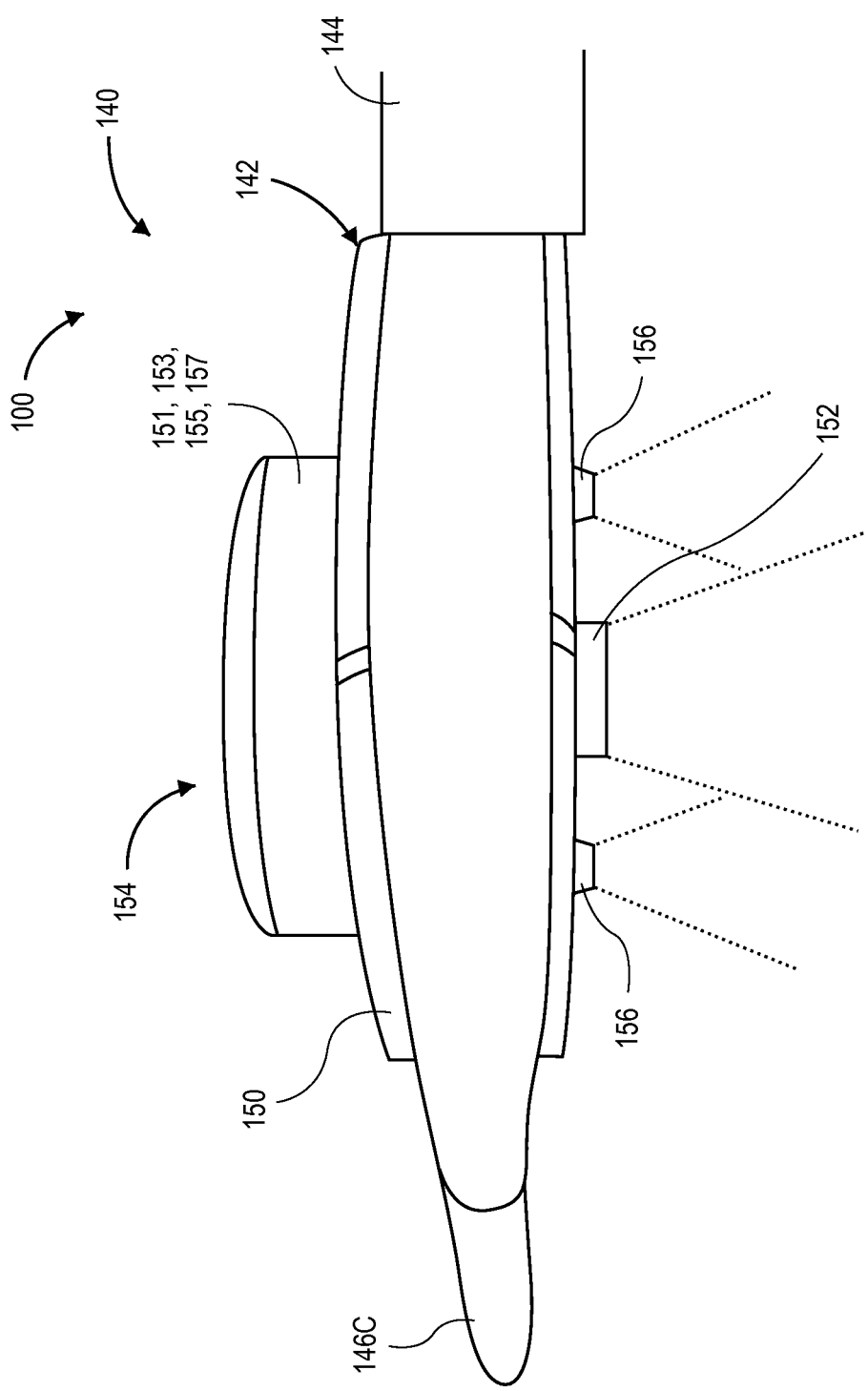

Referring to FIGS. 1A-1D, views of one system 100 including a hand-mounted imaging device are shown. Referring to FIG. 1A, the system 100 includes a worker 140 wearing a glove 150 about his or her left hand 142 and wrist 144. As is shown in FIG. 1A, the glove 150 includes an imaging device 152 (e.g., a digital camera) and a plurality of illuminators 156 provided in a palm, or an anterior, of the hand 142. The glove 150 partially covers fingers 146A, 146B, 146C, 146D and a thumb 146E of the hand 142. Referring to FIG. 1B, the system 100 further includes a display 154 in communication with the imaging device 152 and the illuminators 156 that is provided on a back, or a posterior, of the hand 142. The display 154 further includes a processor 151, a data store 153, a network interface 155 and a power source 157.

Figure 1C:
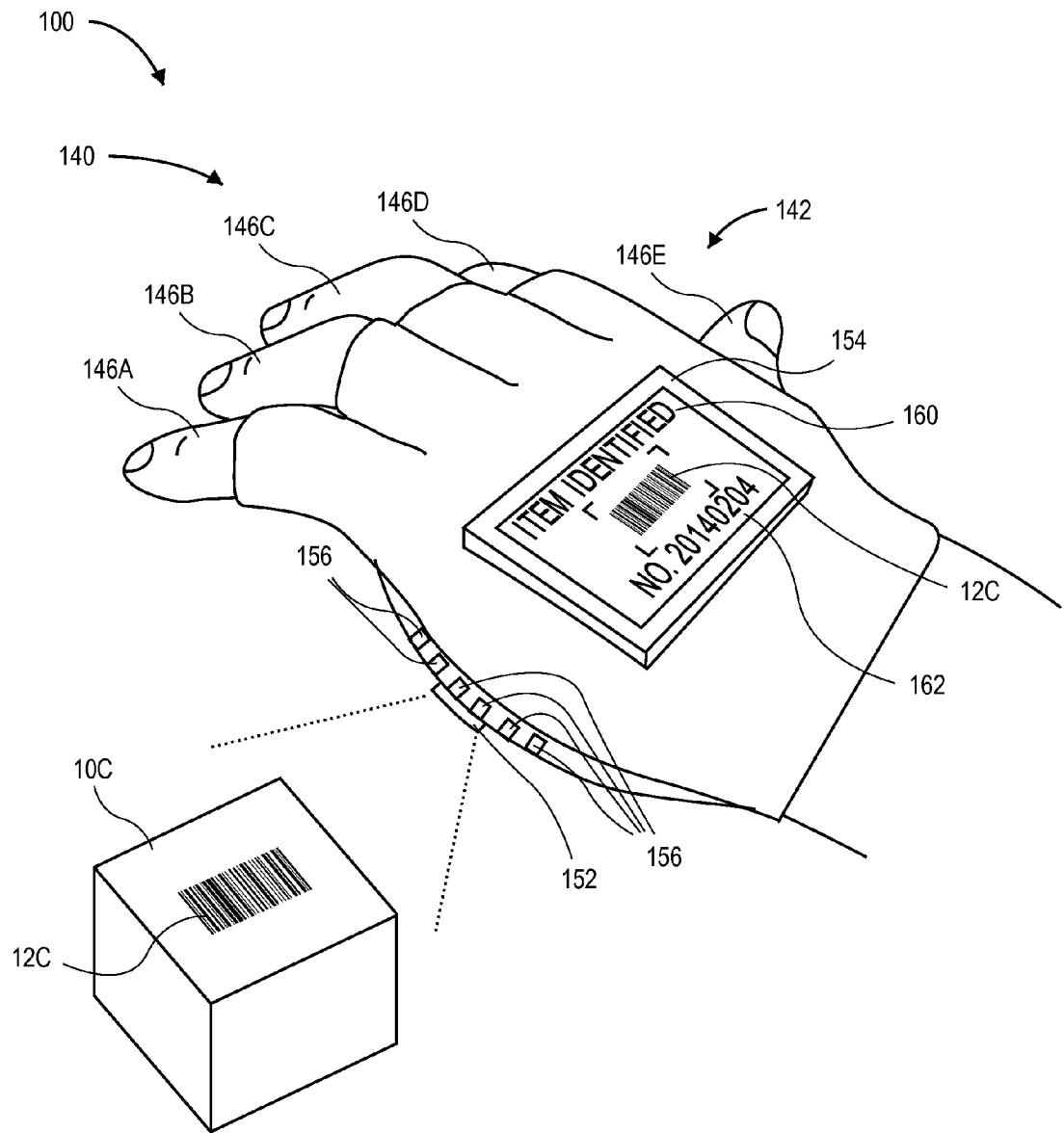

In accordance with some embodiments of the present disclosure, hand-mounted imaging devices may be utilized to capture any type or form of imaging data from a perspective of a human hand, and the imaging data may be utilized for any relevant purpose. Referring to FIG. 1C, the system 100 of FIG. 1A is utilized to capture imaging data regarding an item 10C having a marking 12C (viz., a one-dimensional bar code). At least some of the imaging data may be analyzed to identify the item 10C, e.g., by reading and de-coding the marking 12C, and presented on the display 154. For example, as is shown in FIG. 1C, a message 160 indicating that the item 10C has been identified, and an identification number 162 associated with the item 10C, may be displayed thereon. Accordingly, when the worker 140 wears the glove 150 on a hand 142 and captures imaging data from the item 10C using the imaging device 152 on the palm of the hand 142, relevant information regarding the item 10C, e.g., an image of the marking 12C, a message 160 pertaining to the item 10C, and an identification number 162 of the item 10C, may be displayed on the back of the hand 142, in a convenient location within a field of view of the eyes (not shown) of the worker 140.

Additionally, and also in accordance with embodiments of the present disclosure, hand-mounted imaging devices may be utilized to capture imaging data in close-quartered environments, e.g., one or more digital images at short ranges, particularly those environments where a line of sight between a worker's eyes and subjects of a task with which the worker is associated is occluded. Referring to FIG. 1D, the system 100 of FIG. 1A is utilized to capture imaging data as the worker 140 is performing work on a piece of machinery 10D (viz., an automobile) experiencing a condition 12D (viz., a radiator leakage) that requires attention. Because the condition 12D is obscured from the field of view of the worker 140, the worker 140 is unable to see the condition 12D with his or her eyes. Using the glove 150 and the imaging device 152, the worker 140 may capture imaging data regarding the condition 12D, by raising, lowering, twisting or bending his or her hand 142 and/or the glove 150, as necessary, to place the condition 12D within a field of view of the imaging device 152. In real time or near-real time, or at any subsequent time, the imaging data may be transmitted to and projected upon an external monitor 170, and may thereby enable the worker 140 and others (not shown) to view the condition 12D and relevant portions of the machinery 10D more clearly despite their substantially visually obscured locations. Thus, the hand-mounted networked imaging devices of the present disclosure may aid in the diagnosis of conditions or situations that may be invisible to the eyes, but reachable by one or more hands, which may be used to place an imaging device within a sufficient range of the conditions or situations and to capture relevant imaging data or other multimedia (e.g., still or moving images or accompanying audio signals) of the conditions or situations.

Computer-based systems have revolutionized the manner in which physical transactions involving items are virtually proposed, executed and confirmed. In a fulfillment center environment associated with an electronic marketplace, where hundreds of thousands of items may be received, stored or distributed on a daily basis, the arrival, the receipt, the preparation and the departure of each of the individual items may be tracked by entering information or data into one or more computer systems that may include any number of servers, processors, data stores (e.g., data bases) and input/output peripherals. For example, when an item arrives at a fulfillment center, information or data regarding the item (e.g., an identifier of the item such as a name or a number, as well as a source of the item, and one or more dimensions of the item) and its arrival (e.g., a date and time of the arrival, an identifier of a vehicle or other means by which the item arrived, and an identifier of a worker who unloaded the item from the vehicle or other means) may be captured, recorded and stored on one or more computer systems. Likewise, when an item is stored within a fulfillment center, retrieved from storage, prepared for delivery or shipped to a destination, information or data regarding the persons or manner in which the item is stored, retrieved, prepared or shipped may also be captured, recorded and stored. Similarly, when a task has been performed, one or more workers may type or otherwise enter information or data confirming the performance of the task into one or more computer devices.

Traditionally, information or data has been provided to computer machines by way of a keyboard, keypad or other manual entry device. More recently, however, scanning or reading equipment that is configured to recognize one or more markings or identifiers (e.g., bar codes, alphanumeric characters, images or other symbols) have been applied or affixed onto items, objects, structures or facilities, to decode or otherwise interpret such markings or identifiers, and acknowledge the presence of such items, objects, structures or facilities. The scanners or readers may operate by illuminating dark and light patterns with light and observing the patterns of light reflected therefrom, or by capturing an image of such patterns and interpreting the content thereof through one or more image recognition techniques.

For example, scanners or readers may be used to identify and recognize letters, numbers or other machine-readable representations of data, such as bar codes, or to capture one or more images of a side or facet of an object having a one-dimensional or QR bar code marked therein, and the bar code may be identified or interpreted using one or more formulas or algorithms that are pre-programmed or otherwise trained to recognize such codes. In order to read or interpret a marking such as a bar code using a scanner or reader, however, the item must be positioned within a vicinity of the scanner or reader, and with a specific orientation with respect to an optical element of the scanner or reader, to a particular degree of accuracy or precision. For these reasons, a user who wishes to scan or read a marking, such as a bar code, may be required to exert an inordinate amount of effort that is unrelated to the task for which the reading or interpretation of the bar code is desired. Positioning an item for reading or interpretation by the scanner or reader frequently requires a user thereof to halt or restrict any other activities, in order to concentrate on orienting the item and the scanner or reader correctly. Moreover, depending on the size of the item, as well as the size of the scanner or reader, the physical task of properly orienting the item and the scanner or reader may be daunting as well, particularly in industrial applications or other situations involving heavy items or equipment.

Imaging devices such as digital cameras operate by electronically capturing reflected light from objects and assigning quantitative values to one or more aspects of the reflected light, such as pixels. Unlike a traditional camera, which directs light passing through an optical element toward an array of light-sensitive chemical receptors that are embedded in a film, and exploits the chemical reactions occurring thereon to generate an image associated with the passed light, a digital camera may include one or more sensors having one or more filters associated therewith. The sensors of a digital camera may capture information regarding any number of pixels of the reflected light corresponding to one or more base colors (e.g., red, green or blue) expressed in the reflected light, and store values associated with the pixel colors as one or more data files in a data store or transmit such values to an external computer device for further analysis or reproduction. A digital camera may also include one or more onboard data stores, as well as one or more removable data stores (e.g., stick drives or memory cards), and the data files stored in the one or more data stores may be printed onto paper, displayed on one or more computer displays, or subjected to one or more analyses, such as to identify items expressed therein.

An imaging device may capture one or more images of items within its field of view, which is determined as a function of a distance between a sensor and a lens, viz., a focal length, within the imaging device. Where an object appears within a depth of field, or a distance within the field of view where the clarity and focus is sufficiently sharp, a digital camera may capture light that is reflected off objects of any kind to a sufficiently high degree of resolution using the sensor, and store information regarding the reflected light in one or more data files. In order to enhance the available lighting in a vicinity of a subject from which imaging data is captured by an imaging device, and to thereby increase the amount or change the quality of light reflected from the imaged subject, one or more flash units or other illuminators are commonly provided. Such illuminators may be mounted directly to an imaging device, or provided in a separate structure, and may consist of a single point source, or multiple point sources, which may be programmed or controlled to shine light onto an object in advance of, or simultaneous with, the capturing of images or imaging data therefrom.

Information and/or data regarding features or objects expressed in a digital image may be extracted from the image in any number of ways. For example, a color of a pixel, or a group of pixels in a digital image may be determined and quantified according to one or more standards, e.g., the RGB ("red-green-blue") color model, in which the portions of red, green or blue in a pixel are expressed in three corresponding numbers ranging from 0 to 255 in value, or a hexadecimal model, in which a color of a pixel is expressed in a six-character code, wherein each of the characters may have a range of sixteen. Moreover, a texture of a feature or object expressed in a digital image may be identified using one or more computer-based methods, such as by identifying changes in intensities within regions or sectors of the image, or by defining areas of an image corresponding to specific surfaces. Furthermore, outlines of objects may be identified in a digital image using one or more algorithms or machine-learning tools. For example, some such algorithms or tools may recognize edges, contours or outlines of objects in the digital image, or of portions of objects, and may match the edges, contours or outlines of the objects against a database containing information regarding edges, contours or outlines of known objects.

As is discussed above, and in greater detail below, the present disclosure is directed to the use of hand-mounted networked imaging devices that may be provided on one or more wearable substrates which may be mounted to or otherwise worn on all or portions of the hands and/or wrists of a user. According to some embodiments, the imaging devices may be provided for use anywhere on a hand or a wrist of a user. For example, one or more imaging devices and/or illuminators may be provided in the palms of gloves that are fingered or substantially fingerless, such as the glove 150 of the system 100 of FIGS. 1A-1D, and oriented or configured in one or more desired directions. Alternatively, one or more imaging devices and/or illuminators may be provided in other locations on a user's hands, including but not limited to a back of a hand, as well as one or more fingers, in accordance with the present disclosure.

Additionally, the gloves or other wearable substrates of the present disclosure, or any straps, mounting apparatuses or other features of such gloves or substrates, may be formed from natural or synthetic materials, or from a combination of natural and synthetic materials, including but not limited to leathers, hides, rubbers, vinyls or woven or non-woven fabrics. Such gloves or substrates may be general purpose coverings of the hands or wrists, to which one or more of the imaging devices disclosed herein may be applied, or may be gloves or substrates specifically provided for one or more of the purposes disclosed herein. Further, the imaging devices of the present disclosure may include one or more digital cameras or like sensors of substantially small sizes; for example, the imaging devices may include digital cameras having imaging sensors in the form of a digital charge coupled device and a diameter of less than half an inch. Alternatively, any type or form of imaging device may be incorporated into the gloves or wearable substrates disclosed herein. Additionally, the imaging devices may be associated with such gloves or substrates in any manner, such as by stitching or embedding the imaging devices within the gloves or substrates, or by affixing the imaging devices to the gloves or substrates using one or more glues, adhesives or other bonding agents.

The operation of the imaging devices of the present disclosure may be triggered by any manual or automatic means. For example, such devices may begin operating, or may secure operations, upon a manual activation of an actuator or shutter (e.g., buttons or other points of manual contact provided on the gloves, imaging devices, displays or other portions thereof). Alternatively, the devices may begin operating, or may secure operations, through one or more automatic means. For example, one or more of the imaging devices disclosed herein may be configured to capture imaging data beginning at a predetermined time or within predetermined time intervals (e.g., at 8 o'clock a.m., or between 9 o'clock a.m. and 5 o'clock p.m.) on specific days (e.g., Monday through Friday). The imaging devices may also be configured to sense light characteristics at all times, and to begin capturing imaging data when specific light characteristics are observed (e.g., light intensity levels or colors). For example, when a worker who is wearing one or more of the gloves or substrates disclosed herein, e.g., the glove 140 of FIGS. 1A-1D, opens and closes his or her hands a predetermined number of times, thereby causing light to be temporarily blocked from entering the imaging device, the imaging devices may be configured to sense the alternating periods of lightness and darkness, and to begin or end the capturing of imaging data accordingly. Similarly, the imaging devices may be configured to begin or end the capturing of imaging data after the imaging devices have recognized a specific identifier or marking, e.g., a predetermined bar code. Any means or methods for causing the imaging devices disclosed herein to begin capturing imaging data, or for securing the capturing of imaging data, may be utilized in accordance with the present disclosure.

Moreover, the gloves or substrates may be provided with any number of associated accessories for controlling or enabling the operation of the imaging devices. For example, the gloves or substrates may further include one or more associated speakers, monitors, screens or computer displays, such as the display 154 shown in FIG. 1C, as well as one or more computer processors, memory components, network interfaces, e.g., wired or wireless connections to one or more external networks, and power sources, including but not limited to batteries, solar cells, fuel cells or the like.

Accordingly, the systems and methods of the present disclosure may be utilized to capture imaging data from the perspective of a user's hands, and to present such imaging data to the user, e.g., in the form of still or moving images, and any associated audio signals, or for any other purpose. According to some embodiments, the imaging data may be presented to one or more other users on an external speaker, monitor, screen or computer display, in real time or in near-real time, or may be stored for later use or analysis. In this regard, the imaging data may be used to confirm the performance of one or more tasks, e.g., by identifying information regarding various milestones that may be determined to have been met or accomplished based on the imaging data.

For example, in some embodiments, a worker wearing one or more of the hand-mounted networked imaging devices of the present disclosure may acknowledge the receipt or placement of an item in a particular region or area of a fulfillment center, such as a bin, a cubby, or another storage area. The worker may capture one or more images of a vehicle or a vessel in which the item arrives using a hand-mounted networked imaging device, and the vehicle or vessel may be identified through one or more color-based or photogrammetric analyses of any images, identifiers or markings thereon (e.g., a bar code or text-based identification of the vehicle or vessel), or based on a recognition of the shapes, contours, colors or other characteristics of the vehicle or vessel using the images. Next, the worker may capture one or more images of the item itself, and the item may be identified from one or more identifiers or markings thereon. Finally, the worker may capture one or more images of the region or the area in which the item is to be placed, and the region or the area may be identified from any visible identifiers or markings thereon. Accordingly, after identifying the vehicle or vessel, the item, and the region or the area where the item is placed from images captured using a hand-mounted networked imaging device, the systems and methods of the present disclosure may acknowledge the retrieval of the item from the vehicle and the placement of the item into the region or area within the fulfillment center.

Figure 2A:
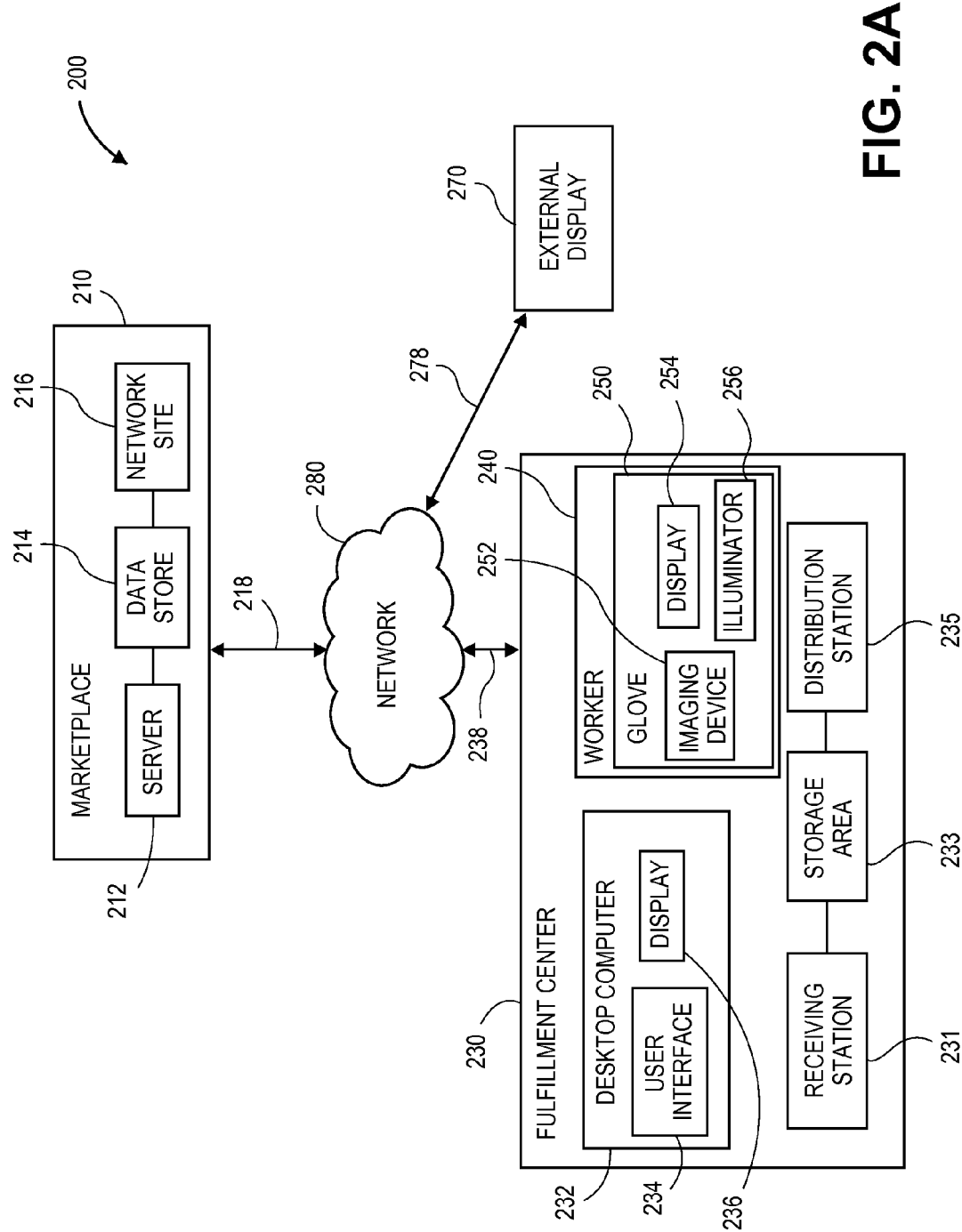
FIGS. 2A and 2B are block diagrams of one system including a hand-mounted networked imaging device, in accordance with embodiments of the present disclosure.
Figure 2B:
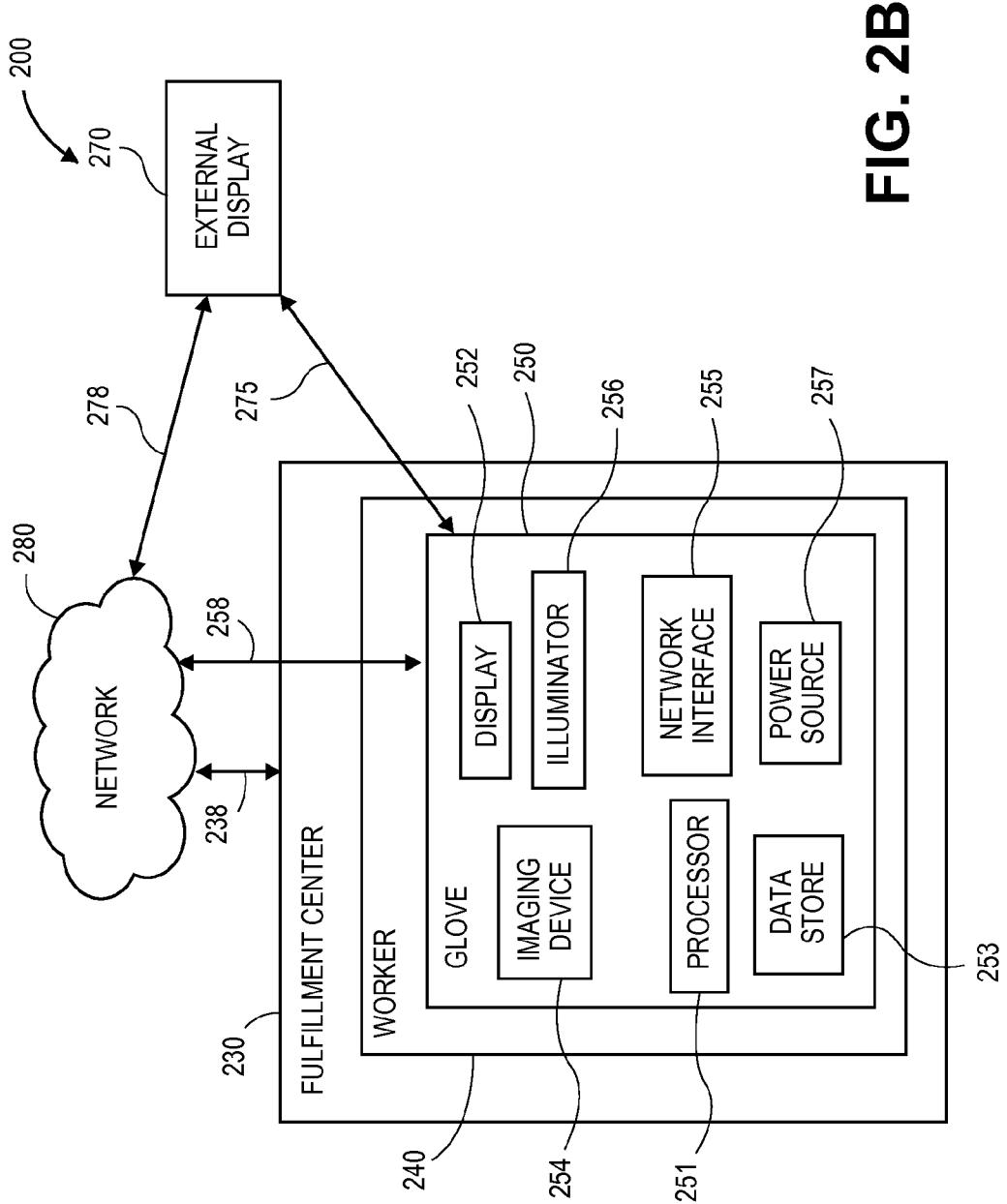

Referring to FIGS. 2A and 2B, block diagrams of one system 200 including a hand-mounted imaging device in accordance with the present disclosure are shown. The system 200 includes a marketplace 210, a fulfillment center 230 and an external display 270 that are connected to one another across a computer network 280, such as the Internet. Except where otherwise noted, reference numerals preceded by the number "2" shown in the block diagrams of FIGS. 2A and 2B indicate components or features that are similar to components or features having reference numerals preceded by the number "1" shown in the system 100 of FIG. 1.

As is shown in FIG. 2A, the marketplace 210 may be any entity or individual that wishes to make items (e.g., goods, services, information or media of any type or form, as well as a package or parcel containing such goods, information or media, or descriptions or accounts of such services) from a variety of sources available for download, purchase, rent, lease or borrowing by customers using a networked computer infrastructure, including one or more physical computer servers 212 and data stores (e.g., databases) 214 for hosting a network site 216. The marketplace 210 may be physically or virtually associated with one or more storage or distribution facilities, such as the fulfillment center 230. The web site 216 may be implemented using the one or more servers 212, which connect or otherwise communicate with the one or more data stores 214 as well as the network 280, as indicated by line 218, through the sending and receiving of digital data. Moreover, the data stores 214 may include any type of information regarding items that have been made available for sale through the marketplace 210, or ordered by customers from the marketplace 210, or any type of information regarding items that have been received at, stored in, or delivered from, the fulfillment center 230.

The fulfillment center 230 may be a facility or complex that is adapted to receive, store, process and/or distribute items on behalf of the marketplace 210. As is shown in FIG. 2A, the fulfillment center 230 may operate one or more order processing and/or communication systems using a computing device such as a desktop computer 232 having a display 236 and/or software applications having one or more user interfaces 234 (e.g., a browser or other dedicated application), or through one or more other computing machines that may be connected to the network 280, as is indicated by line 238, in order to transmit or receive information in the form of digital or analog data, or for any other purpose. The desktop computer 232 may also operate or provide one or more interfaces, such as the user interface 234, for receiving interactions (e.g., text, numeric entries or selections) from one or more operators, users or workers in response to such information or data.

The fulfillment center 230 may also include a receiving station 231, a storage area 233 and a distribution station 235. The receiving station 231 may include any apparatuses that may be required in order to receive shipments of items from one or more sources and/or through one or more channels, including but not limited to docks, lifts, cranes, jacks, belts or other conveying apparatuses for obtaining items and/or shipments of items from carriers such as cars, trucks, trailers, freight cars, container ships or cargo aircraft, and preparing such items for storage or distribution to customers. The storage area 233 may include one or more predefined two-dimensional or three-dimensional spaces for accommodating items and/or containers of such items, such as aisles, rows, bays, shelves, slots, bins, racks, tiers, bars, hooks, cubbies or other like storage means, or any other appropriate regions or stations. The distribution station 235 may include one or more regions or stations where items that have been retrieved from a designated storage area may be evaluated, prepared and packed for delivery to addresses, locations or destinations specified by customers.

The fulfillment center 230 may further include one or more control systems that may generate instructions for conducting operations at one or more of the receiving station 231, the storage area 233 or the distribution station 235, which may be associated with the desktop computer 232 or one or more other computing machines, and may communicate with the marketplace 210 or the worker 240 over the network, as indicated by line 238, through the sending and receiving of digital data.

The fulfillment center 230 may also include one or more workers or staff members, such as the worker 240, for handling or transporting items within the fulfillment center 230, such as from a car, truck, ship or aircraft to a crane, jack, belt or another conveying apparatus at the receiving station 231 to a shelf, bin, rack, tier, bar, hook or other storage means within the storage area 233, or to a defined region within the distribution station 235. Moreover, the worker 240 may operate one or more computing devices for registering the receipt, retrieval, transportation or storage of items within the fulfillment center, which may be a device that is specifically programmed or adapted for such purposes, or a general purpose device such a personal digital assistant, a digital media player, a smartphone, a tablet computer or a laptop computer, and may include any form of input and/or output peripherals such as scanners, readers, keyboards, keypads, touchscreens or pointing devices.

As is shown in FIG. 2A, the worker 240 may wear and operate a glove 250 including a hand-mounted networked imaging device 252, a display 254 and one or more illuminators 256 mounted thereon. The glove 250 may be a wearable mounting apparatus or article of apparel covering all or a portion of a hand of the user 240, i.e., all or portions of the posterior and/or the anterior of the hand, and providing one or more sufficiently sized surfaces or platforms for mounting the imaging device 252, the display 254 and/or the illuminators 256 and enabling the worker 240 to wear the imaging device 252 about his or her hand. As with the glove 150 shown in FIGS. 1A-1D, the glove 250 may be substantially fingerless, although any form of glove, including a glove which covers more or less of a hand of a worker 240 than the glove 150 of FIGS. 1A-1D (e.g., gloves which completely cover one or more fingers), may be utilized for enabling the worker 240 to functionally wear the imaging device 252 in accordance with the present disclosure. Moreover, those of ordinary skill in the pertinent art will recognize that the various components within the glove 250 may be physically or functionally joined by one or more wired or wireless means, and that the glove 250 may include one or more connectors or conductors (not shown) as may be required.

The imaging device 252 may be any type or form of optical recording device that may be provided for the purpose of capturing one or more images or sets of imaging data within the fulfillment center 230. The imaging device 252 may include or comprise any form of optical recording device (e.g., a digital camera, scanner or other device) for identifying markings such as codes, text, numbers, symbols, trademarks, shapes, images, outlines or figures of any breadth, width or density, and generating an electrical output corresponding the captured markings. The imaging device 252 may transfer the electrical output to one or more processors, data stores or other system components, e.g., via the network 280, where the electrical output may be decoded and interpreted, and subsequently utilized in one or more applications, such as to acknowledge or register an item with which the markings are associated. Additionally, the imaging device 252 may be adapted to capture images about any axis and in any plane.

The imaging device 252 may further include an actuator, a shutter or any other operational components for initiating or securing the operation of the imaging device 252, and may be configured to capture imaging data in the form of one or more still or moving images, as well as any relevant audio signals or other information. The imaging device 252 may be configured to capture and store images for subsequent transmission to an external device, e.g., over the network 280, at a later time, or to store and transmit such images to the external device in real time, or in near-real time, and in a synchronous or asynchronous manner, depending on the applications in which the corresponding systems and methods are used.

Additionally, the imaging device 252 may be mounted to the glove 250 in any manner, e.g., by stitching, sewing, adhering, gluing or otherwise affixing the imaging device 252 thereto. Alternatively, the imaging device 252 may be releasably joined to the glove 250 by any universal means, such as a standard hook-and-loop fastening system (e.g., Velcro®), or a stitched frame or other mounting feature, that may be known to those of ordinary skill in the pertinent art. For example, by enabling the imaging device 252 to be releasably joined to the glove 250, the systems and methods of the present disclosure permit the imaging device 252 to be utilized by multiple workers 240 who may have differently sized hands, and may thus require differently sized gloves 250, or for workers who may desire to wear a different glove 250 from their co-workers (e.g., for sanitary reasons).

Alternatively, or instead of the glove 250, one or more wearable substrates may be provided for the purpose of mounting the imaging device 252 about the metacarpal bones of the hand using one or more straps or other like features, which may be formed from any suitable synthetic or natural materials such as leather, cloth, fabric, nylon or elastics, and joined together using any type of fastener, including buckles, snaps or hook-and-loop fasteners. Any type of wearable substrates may be provided in order to enable the worker 240 to wear the imaging device 252 accordance with the present disclosure.

Preferably, the imaging device 252 is provided on a palm, or an anterior, of the glove 250, e.g., the imaging device 152 of the glove 150 of FIG. 1A. Alternatively, however, the imaging device 252 may be provided on any other portion of the glove 250, including on a back, or a posterior, of the glove 250, as well as on one or more fingers or portions thereof of the glove 250. Moreover, although the system 200 shown in FIG. 2A includes a single imaging device 252, those of ordinary skill in the pertinent arts will recognize that any number or type of imaging devices 252 (e.g., cameras) may be provided on the glove 250 in accordance with the present disclosure.

The display 254 may be any type or form of display device or apparatus configured to provide any form of information regarding one or more tasks to be performed by the worker 240, as well as any operations of the glove 250, the imaging device 252 or any related components. For example, as is shown in FIG. 1C, the display 254 may provide information or data regarding images or imaging data captured by the imaging device 252, as well as any relevant instructions for the worker 240, including an identification of any items, objects, structures or facilities having identifiers or markings to be scanned or read, or locations of the specific items, objects, structures or facilities, or any other relevant information or data. Moreover, the display 254 may include any type of display element, including a liquid crystal display (or "LCD"), a touchscreen display (e.g., a capacitive or resistive touchscreen), an E-ink display, a light emitting diode (or "LED") display, such an organic light emitting diode (or "OLED") display, or any other form of display element.

The illuminators 256 may be any form of flash or other light source that may be independently operated on short order, by way of one or more commands. For example, the illuminators 256 may include one or more LED lights arranged at a single point, in a line or strip, in an array or in one or more polygonal arrangements or configurations (e.g., shapes), such as the circular or dodecagonal arrangement of the illuminators 156 of the glove 150 shown in FIG. 1A. Such LED lights, or LEDs, may include one or more diodes that are housed within a transparent plastic bulb or canister-like housing and configured to direct a comparatively large amount of light-based energy for release through the housing. The illuminators 256 may be controlled concurrently or independently with regard to the imaging device 252 based on one or more independently targeted control signals received from a hardware component or software interface operating on or associated with one or more computing devices. Additionally, the illuminators 256 may be provided in a single color, or in multiple colors, and at any level of intensity.

As is also shown in FIG. 2A, an external display 270 is provided. Like the display 254, the external display 270 may be any type or form of display device or apparatus configured to provide any form of information regarding one or more tasks being performed by the worker 240, or any relevant operations of the glove 250, the imaging device 252, the display 254 or any related components. The external display 270 may receive any type or form of imaging data or other information, including but not limited to still or moving images and any associated audio signals, e.g., digital or analog data, from one or more other computing machines that may be connected to the network 280, as is indicated by line 278. Also like the display 254, the external display 270 may include any type of display element, including an LCD, a touchscreen display (e.g., a capacitive or resistive touchscreen), an E-ink display, an LED display, e.g., an OLED display, or any other form of display element.

Referring to FIG. 2B, additional features of the glove 250 of FIG. 2A are shown in greater detail. As is shown in FIG. 2B, the glove 250 further includes at least one computer processor 251, at least one data store 253, a network interface 255 and a power source 257, e.g., a battery or other source of power. The processor 251 may be configured to operate any number of elements, components or features for capturing and interpreting one or more images of any kind using the imaging device 252, and for analyzing, interpreting or recognizing any type or form of marking (e.g., codes, text, numbers, symbols, trademarks, shapes, outlines or figures) that may be known to those of ordinary skill in the pertinent art, as well as any type of computing elements, components or features that may be required to capture or interpret such images.

Additionally, as is also shown in FIG. 2B, the imaging device 252 and the other components of the glove 250 may be connected to the network 280 by any wired or wireless means either indirectly through the fulfillment center 230, or directly by way of the network interface 255, as is indicated by line 258, or one or more other relevant components. Likewise, the glove 250 may be connected to the external display 270 via the network 280 by any wired or wireless means, or by way of the network interface 255, as is indicated by line 275. For example, the network interface 255 may connect the glove 250 and/or the imaging device 252 to the network 280 and/or to the external display by a hardwired or physical connection (e.g., a Universal Serial Bus, or "USB," connection), a short-range wireless connection (e.g., according to Bluetooth® or another protocol) or a standard wireless fidelity (or "WiFi") connection. The power supply 257 may include any means for providing necessary power to the glove 250, the imaging device 252 or one or more other components provided thereon, including one or more batteries, cells, capacitors or other power-generating components, as well as one or more wired or wireless connections to an external power source. The power supply 257 may operate using alternating current (AC) or direct current (DC), and may be energized and/or charged by any means known to those of ordinary skill in the pertinent art, including a wired connection to the external power source, or through a wireless charging connection such as an inductive charging system providing an electromagnetic field and/or an inductive coupling between a base station (not shown) and the power supply 257.

The computers, servers, devices and the like described herein have the necessary electronics, software, memory, storage, databases, firmware, logic/state machines, microprocessors, communication links, circuits or circuit boards, displays or other visual or audio user interfaces, printing devices, and any other input/output interfaces in order to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, link, node, hub or any other aspect of the present disclosure.

Those of ordinary skill in the pertinent arts will understand that process steps described herein as being performed by a "marketplace," a "fulfillment center," a "worker" or an "imaging device" may be automated steps performed by their respective computer systems which may be dedicated to the performance of such steps, or implemented within software modules (or computer programs) executed by one or more general purpose computers. Moreover, process steps described as being performed by a "marketplace," a "fulfillment center," a "worker" or an "imaging device" may be typically performed by a human operator, but could, alternatively, be performed by an automated agent.

The marketplace 210, the fulfillment center 230 and/or the worker 240 may use any web-enabled or Internet applications or features, such as the user interface 234, or any other client-server applications or features including electronic mail (or E-mail), or other messaging techniques, to connect to the network 280 or to communicate with one another, such as through short or multimedia messaging service (SMS or MMS) text messages. For example, in addition to the desktop computer 232, or the imaging device 252, those of ordinary skill in the pertinent art would recognize that the marketplace 210, the fulfillment center 230 and/or the worker 240 may operate any of a number of computing devices that are capable of communicating over the network, including but not limited to set-top boxes, personal digital assistants, digital media players, web pads, smartphones, laptop computers, desktop computers, electronic book readers, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or servers, such as the server 212, the desktop computer 232, the imaging device 252, or any computers or control systems utilized by the marketplace 210, the fulfillment center 230 or the worker 240 and having sequences of instructions which, when executed by a processor (such as a central processing unit, or CPU), cause the processor to perform all or a portion of the functions, services and/or methods described herein. Such computer executable instructions, programs, software and the like may be loaded into the memory of one or more computers using a drive mechanism associated with the computer readable medium, such as a floppy drive, CD-ROM drive, DVD-ROM drive, network interface, or the like, or via external connections.

Some embodiments of the systems and methods of the present disclosure may also be provided as a computer executable program product including a non-transitory machine-readable storage medium having stored thereon instructions that may be used to program a computer (or other electronic device) to perform processes or methods described herein. The machine-readable storage medium may include, but is not limited to, hard drives, floppy diskettes, optical disks, CD-ROMs, DVDs, read-only memories (ROMs), random access memories (RAMs), erasable programmable read-only memories (EPROMs), electrically erasable programmable read-only memories (EEPROMs), flash memory, magnetic or optical cards, solid-state memory devices, or other types of media/machine-readable medium that may be suitable for storing electronic instructions. Further, embodiments may also be provided as a computer executable program product that includes a transitory machine-readable signal. Examples of machine-readable signals, whether modulated using a carrier or not, may include, but are not limited to, signals that a computer system or machine hosting or running a computer program can be configured to access, or including signals that may be downloaded through the Internet or other networks.

For the purposes of illustration, some of the systems and methods disclosed herein may be referenced primarily in the context of a glove having a single imaging device disposed thereon that may be worn by one or more workers in a fulfillment center environment, such as the glove 150 worn by the worker 140 shown in FIGS. 1A through 1D. As will be recognized by those of skill in the art, however, the systems and methods disclosed herein may also be used in many other situations, and their utility is not limited to any of the preferred embodiments described herein.

Figure 3:
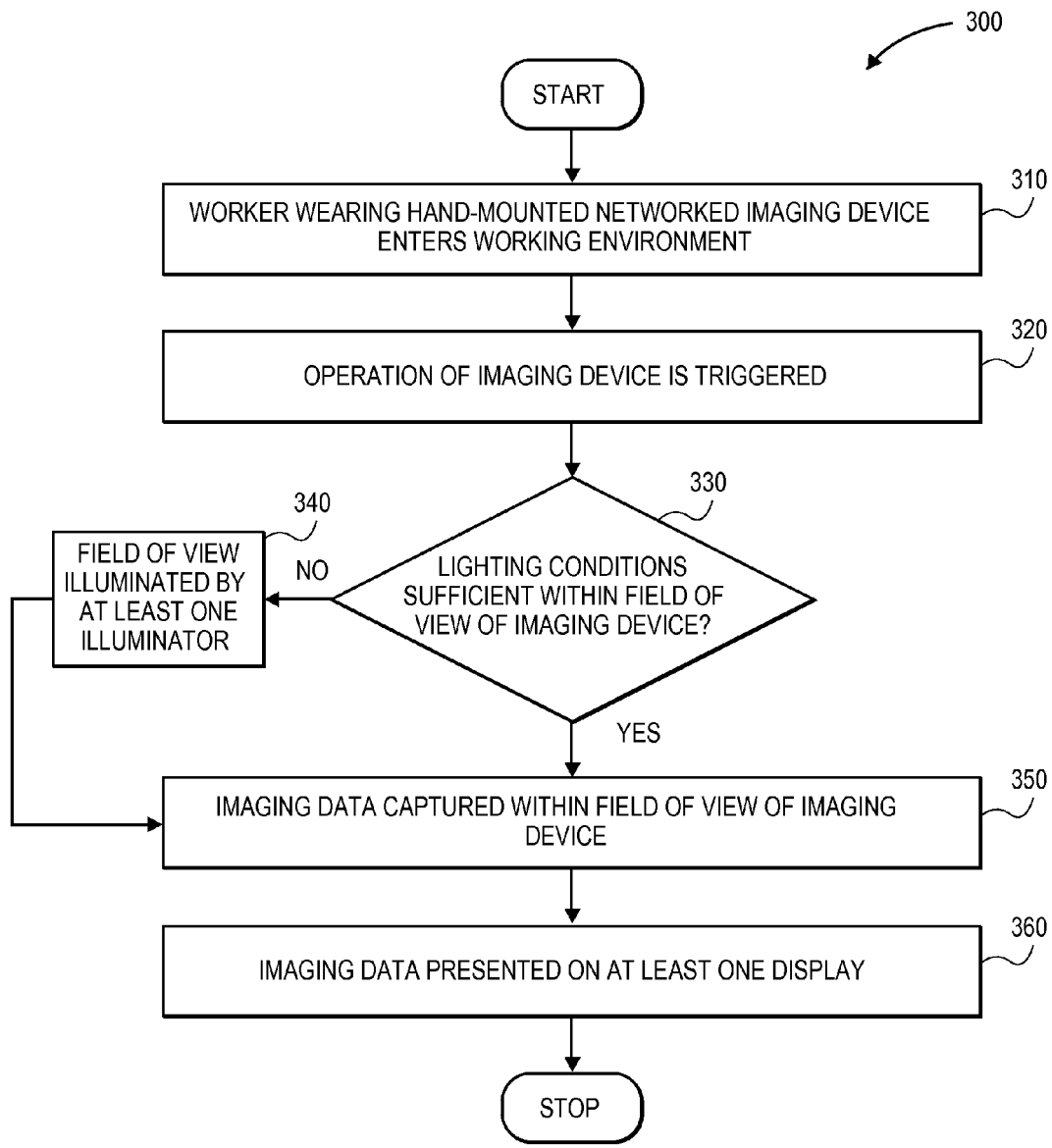
FIG. 3 is a flow chart of one process utilizing a hand-mounted networked imaging device, in accordance with embodiments of the present disclosure.

As is discussed above, some embodiments of the present disclosure are directed to the use of a hand-mounted networked imaging device to capture imaging data, e.g., one or more digital images, and to display the imaging data on one or more monitors or displays, or to store, process or analyze the imaging data for any relevant purpose. Referring to FIG. 3, a flow chart 300 of one process that utilizes a hand-mounted networked imaging device in accordance with embodiments of the present disclosure is shown. At box 310, a worker wearing a hand-mounted networked imaging device enters a working environment. For example, the worker may wear an article of clothing about his or her hand having an imaging device provided thereon, e.g., the glove 150 of FIGS. 1A-1D.

At box 320, the operation of the imaging device is triggered. For example, the imaging device may be configured to operate upon a manual or automatic operation of an actuator, or to begin capturing imaging data at a specific time. Alternatively, the imaging device may be configured to begin operating after the presence of the imaging device is sensed within a given environment. At box 330, whether the lighting conditions are sufficient within a field of view of the imaging device is determined. For example, a level of light sensed by an imaging sensor of the imaging device may be compared to a threshold level.

If the lighting conditions are not sufficient, then the process advances to box 340, where the field of view is illuminated by at least one illuminator. Referring again to FIG. 1A, one or more illuminators 156 may be provided in a vicinity of the imaging device 152, and aligned to cast light into or within the field of view of the imaging device 152, as needed. After the field of view of the imaging device is illuminated by at least one illuminator, or if the lighting conditions within the field of view are sufficient, then the process advances to box 350, where imaging data is captured from within the field of view of the imaging device. At box 360, at least some of the imaging data is presented on at least one computer display, and the process ends. For example, referring again to FIGS. 1C and 1D, the imaging data may be displayed on the display 152 provided on the posterior of the glove 150, or on the external display 170, or on any other computer display device. Alternatively, or additionally, the imaging data may be stored in one or more data stores, or transmitted to one or more other computer devices by way of a network, or subject to one or more analyses.

Figure 4:
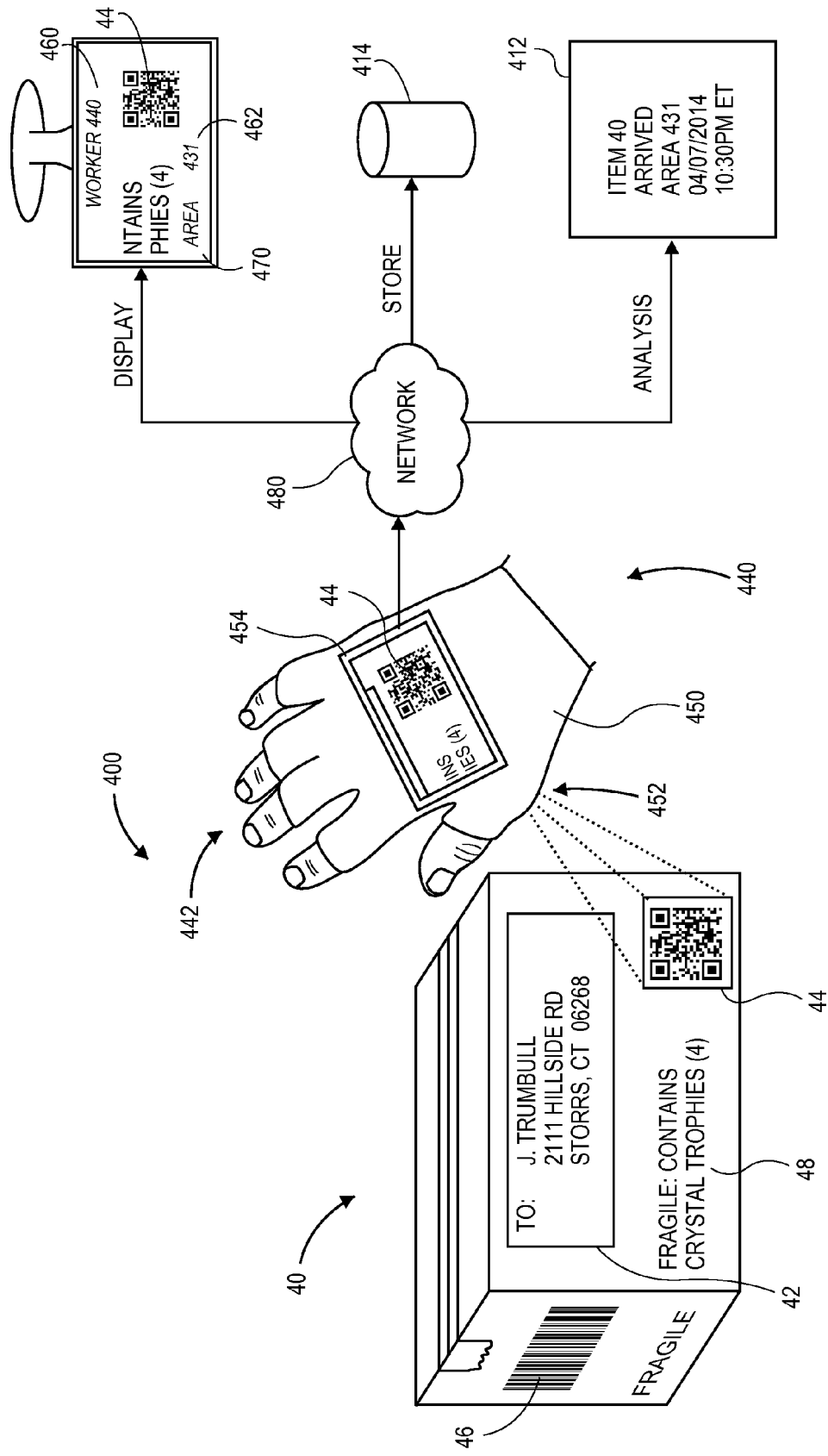
FIG. 4 is a view of one system including a hand-mounted networked imaging device, in accordance with embodiments of the present disclosure.

Therefore, in accordance with embodiments of the present disclosure, a hand-mounted networked imaging device may capture imaging data from the perspective of a user's hands, and the captured imaging data may be utilized for any relevant purpose. Referring to FIG. 4, a view of one system 400 including a hand-mounted networked imaging device in accordance with embodiments of the present disclosure is shown. Except where otherwise noted, reference numerals preceded by the number "4" in FIG. 4 indicate components or features that are similar to components or features having reference numerals preceded by the number "2" in FIG. 2A or 2B, or components or features having reference numerals preceded by the number "1" shown in FIGS. 1A-1D.

As is shown in FIG. 4, a worker 440 who is wearing, on his or her hand 442, a glove 450 having an imaging device 452 provided thereon may capture imaging data regarding an item 40 (e.g., a parcel) having a shipping label 42, a two-dimensional bar code 44, a one-dimensional bar code 46 and a description 48 on surfaces thereof. The imaging device 452 is configured to transmit some or all of the imaging data captured from the item 40 to a network 480.

In accordance with the present disclosure, imaging data captured using a hand-mounted networked imaging device may be utilized for any purpose. As is shown in FIG. 4, the imaging data may be displayed on display 454 of glove 450, and/or may be transmitted from the imaging device 452 to a computer display 470 and displayed thereon, to one or more data stores 414 for storage therein, or to one or more servers 412 for analysis. For example, as is shown in FIG. 4, information shown on the display 470 may include identifiers 460, 462 of the worker 440 and his or her location, as well as at least some of the imaging data captured by the imaging device 452, including the two-dimensional bar code 44 and at least a portion of the shipping label 42. By displaying such information on the display 470, the systems and methods disclosed herein permit others, in addition to the worker 440, to monitor the work performed by the worker 440 from the perspective of his or her hands. Likewise, as is also shown in FIG. 4, the imaging data may be stored in at least one data store 414, and subsequently recalled at a later time. Finally, the imaging data may be provided to a server 412 or other computer device, along with any other data or metadata, such as a time or date at which the imaging data was captured, for analysis, auditing or review.

The systems and methods of the present disclosure may also utilize hand-mounted networked imaging devices, and the imaging data captured thereby, in order to confirm the performance of one or more tasks. For example, the imaging data may be processed to recognize indicia of one or more events or circumstances from the imaging data, and to record the occurrence of such events or circumstances in one or more data stores. The completion of a predetermined task comprising a plurality of such events or circumstances may thus be confirmed using the imaging data captured using one or more of the hand-mounted networked imaging devices in accordance with the present disclosure.

Figure 5:
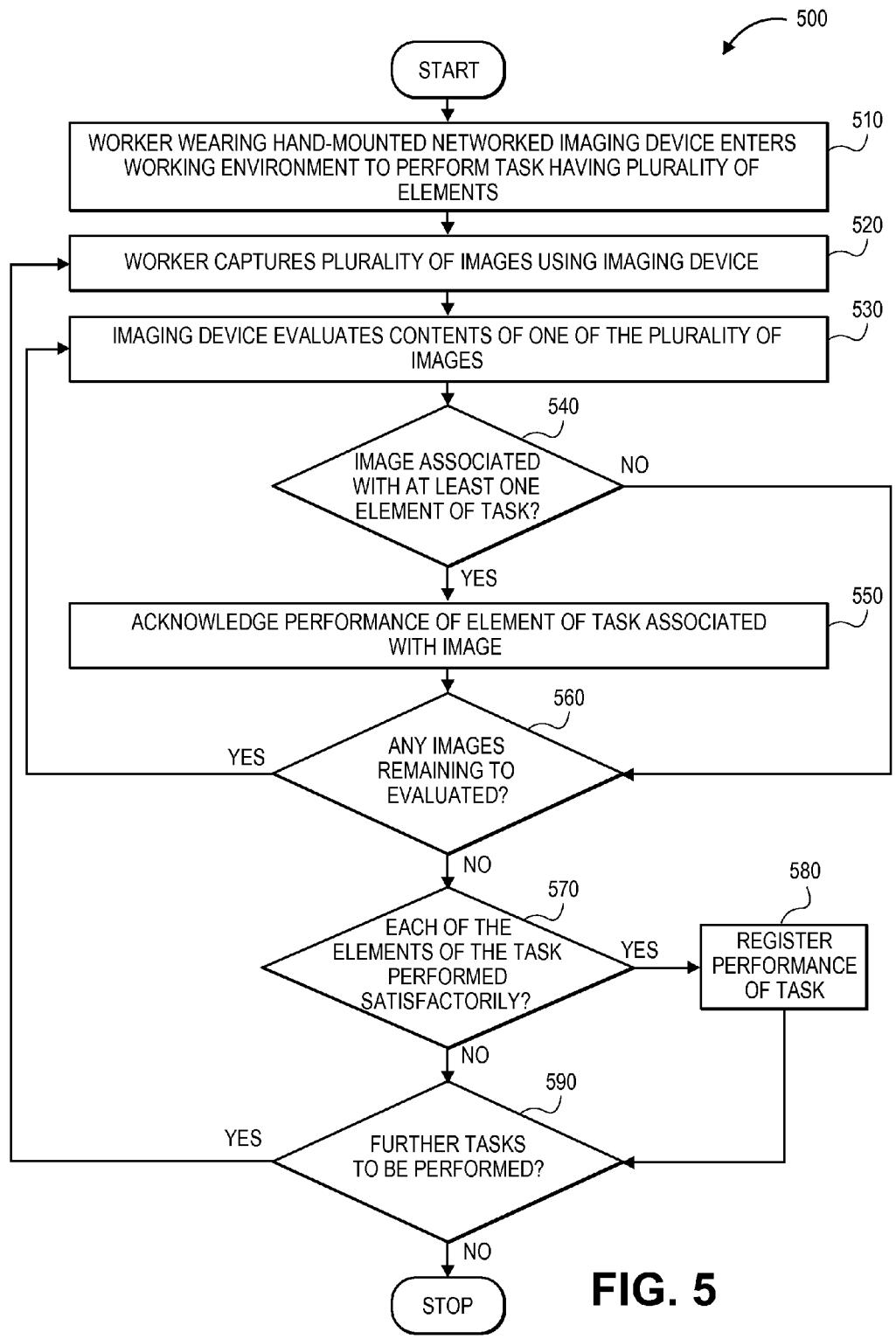
FIG. 5 is a flow chart of one process utilizing a hand-mounted networked imaging device, in accordance with embodiments of the present disclosure.

Referring to FIG. 5, a flow chart 500 of one process that utilizes a hand-mounted networked imaging device in accordance with embodiments of the present disclosure is shown. At box 510, a worker wearing a hand-mounted networked imaging device enters a working environment in order to perform a task having a plurality of elements. The task may be any type or form of basic or complex evolution requiring a number of discrete steps or events to be performed in series or in parallel. At box 520, the worker captures a plurality of images using the imaging device. For example, referring again to FIGS. 1A-1D, a worker 140 wearing the glove 150 may capture one or more images of the item 10C or the marking 12C shown in FIG. 1C, or of the piece of machinery 10D or the condition 12D shown in FIG. 1D, or the various surroundings, using the imaging device 152. Similarly, referring again to FIG. 4, a worker 440 wearing the glove 450 may capture one or more images of the item 40, including but not limited to images of the shipping label 42, the bar codes 44, 46 or the description 48 of the item 40, as well as one or more images of the environment in which the item 40 is provided (e.g., images of any objects, structures or facilities in a vicinity of the item 40, or images of other items).

At box 530, the imaging device evaluates the contents of one of the plurality of images. For example, the imaging device may process a selected one of the plurality of images to identify any relevant information or data therein, including but not limited to any edges, contours or outlines of objects in the image, or of portions of objects, and may identify one or more items, objects, structures or facilities within a field of view of the imaging device based on information regarding such edges, contours or outlines of the objects that may be stored in one or more data stores. Alternatively, the contents of the images may be compared to contents of other images that may be stored in one or more data stores.

At box 540, whether the image may be associated with at least one element of the task is determined. For example, the task may require travel to a location, operation of a machine, or manipulation of an object, and the evaluation of the image at box 530 may be directed to determining whether the image includes any indicator or evidence that the worker traveled to the location, operated the machine or manipulated the object expressed therein. If the image is associated with at least one element of the task, then the process advances to box 550, where the performance of the element of the task with which the image is associated is acknowledged.

If the image is determined to not be associated with at least one element of the task, or after the association of the image with the at least one element of the task is acknowledged, the process advances to box 560, where whether any additional images of the plurality of images captured at box 520 require evaluation. If at least one of the images has not yet been evaluated, then the process returns to box 530, where the contents of another of the images is evaluated. If the content of each of the images has been evaluated, however, then the process advances to box 570, where it is determined whether each of the elements of the task that the worker was charged with completing has been satisfactorily performed. For example, if the content of the plurality of the images includes evidence or indicia that each of the plurality of elements included in the task identified at box 510 has been performed, then the task itself may be deemed to have been satisfactorily performed. If the plurality of images does not include evidence or indicia that at least one of the plurality of elements has been performed, however, then the task as a whole may not be confirmed as having been satisfactorily performed. Further evaluation as to whether the task has actually been performed, or why one or more elements of the task have not been satisfactorily performed, may be required.

If each of the elements of the task has been performed, then the process advances to box 580, where the performance of the task is registered, e.g., in a record maintained in at least one data store. If each of the elements of the task has not been performed, or after the performance of the task has been registered, then the process advances to box 590, where it is determined whether any further tasks are required of the worker. If any such tasks are required, then the process returns to box 520, where the worker captures another plurality of images. If no such tasks are required, however, then the process ends.

Those of ordinary skill in the pertinent arts will recognize that the systems and methods of the present disclosure may capture, analyze, display and/or store digital images or other imaging data at any time and in any order, and that the systems and methods disclosed herein are not limited to the order in which the boxes are provided in the flow chart 500 of FIG. 5. For example, an imaging device may capture and analyze images in series or in parallel, in real time or in near-real time, and singly or in one or more batch processing operations. Moreover, the images may be captured and analyzed automatically or in response to one or more manual instructions. Further, the images or imaging data may be selected for storage or display on any basis.

Figure 6:
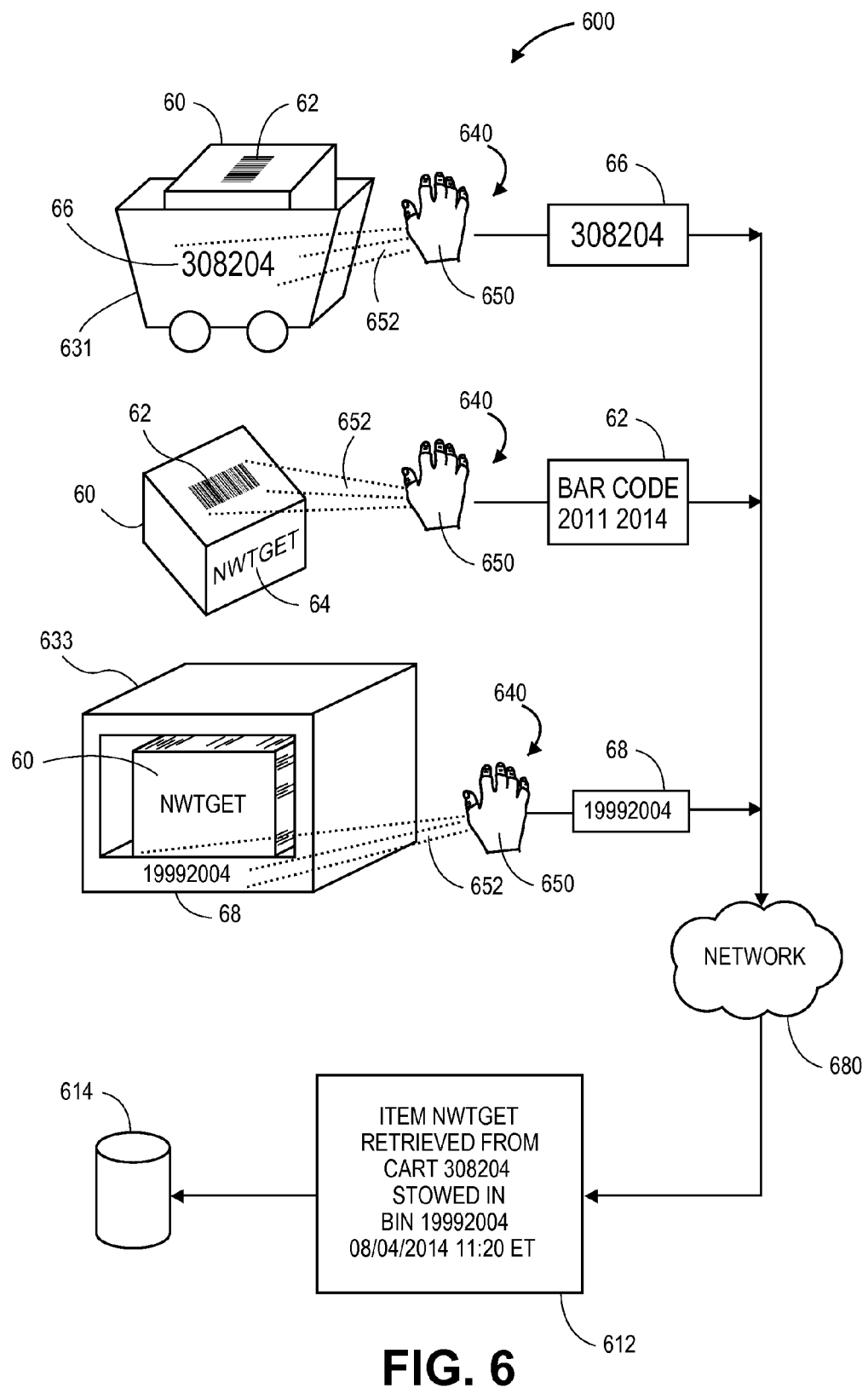
FIG. 6 is a view of one system including a hand-mounted networked imaging device, in accordance with embodiments of the present disclosure.

A determination as to whether each of the elements of a task has been performed based on imaging data captured using a hand-mounted networked imaging device of the present disclosure may be conducted in series or in parallel, and based on evaluation of a single set of imaging data (e.g., a single image) captured using the hand-mounted networked imaging device, or multiple such sets (e.g., multiple images). Referring to FIG. 6, a view of one system 600 including a hand-mounted networked imaging device in accordance with embodiments of the present disclosure is shown. Except where otherwise noted, reference numerals preceded by the number "6" in FIG. 6 indicate components or features that are similar to components or features having reference numerals preceded by the number "4" in FIG. 4, by the number "2" in FIG. 2A or 2B, or components or features having reference numerals preceded by the number "1" shown in FIGS. 1A-1D.

As is shown in FIG. 6, the system 600 includes an item 62, a vehicle 631 (e.g., a cart), and a bin 633. The item 62 includes identifiers 62, 64 in the form of a one-dimensional bar code 62 and a label 64 thereon. The vehicle 631 includes an identification number 66 provided on an external surface thereof. The bin 633 also includes an identification number 68 provided on an external surface thereof. A worker 640 wearing a glove 650 that includes a hand-mounted networked imaging device 652 and is connected to a network 680 may capture imaging data from the item 60, the cart 631 or the bin 633 using the hand-mounted networked imaging device 652, including but not limited to imaging data regarding one or more of the bar code 62, the label 64, the identifier 66 or the identifier 68.

As is discussed in greater detail above, and in accordance with the present disclosure, the performance of a task may be confirmed by evaluating one or more images or sets of imaging data to determine whether each of the steps, elements or other aspects required in order to complete the task have been successfully performed. For example, where the worker 640 of FIG. 6 is instructed to remove the item 60 from the vehicle 631 and to place the item 60 in the bin 633, the performance of the task may be confirmed based on one or more images or sets of imaging data regarding the item 60, the vehicle 631 and the bin 633. First, the vehicle 631 may be identified by recognizing the numbers expressed in the identifier 66 (viz., 308204) provided on an external surface thereof in one or more images or sets of imaging data captured using the hand-mounted networked imaging device 652. Second, the item 60 itself may be identified by reading and decoding the bar code 62 (viz., bar code no. 20112014), or, alternatively, by recognizing the label 64, using one or more images or sets of imaging data captured using the hand-mounted networked imaging device 652. Finally, the bin 633 may be identified by recognizing the identifier 68 (viz., 19992004) provided on an external surface thereof in one or more sets of imaging data captured using the hand-mounted networked imaging device 652.

Therefore, based on the identification of the vehicle 631 in which the item 60 arrived, the identification of the item 60 itself, and the identification of the bin 633 into which the item 60 is to be deposited based on imaging data captured using one or more hand-mounted networked imaging devices of the present disclosure, the placement of the item 60 within the bin 633 by the worker 640 may be confirmed quickly and efficiently without requiring the worker 640 to exert any significant additional effort other than to orient his or her hands 640 toward the bar code 62, the label 64, the identifier 66 or the identifier 68.

Although the disclosure has been described herein using exemplary techniques, components, and/or processes for implementing the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure. For example, although many of the embodiments described herein or shown in the accompanying figures refer to providing imaging devices and illuminators on palms of fingerless gloves, the systems and methods disclosed herein are not so limited, and may be utilized in connection with imaging devices and/or illuminators that may be mounted to or associated with any type or form of glove or other wearable substrate that may be worn about any portion of a user's hand.

More specifically, those of ordinary skill in the pertinent arts will recognize that the systems and methods of the present disclosure may be utilized to determine whether any type or form of task has been sufficiently performed, and are not limited to acknowledging movements of items within a fulfillment center environment. Furthermore, the systems and methods of the present disclosure may also determine whether a discrete element of a task has been performed, or whether a task has been performed in its entirety, based on a single image or set of imaging data, or based or on one or more images or sets of imaging data. Additionally, those of ordinary skill in the pertinent art will also recognize that aspects, features, components or parts of the various embodiments disclosed herein are interchangeable and may be used in connection with one or more other embodiments.

It should be understood that, unless otherwise explicitly or implicitly indicated herein, any of the features, characteristics, alternatives or modifications described regarding a particular embodiment herein may also be applied, used, or incorporated with any other embodiment described herein, and that the drawings and detailed description of the present disclosure are intended to cover all modifications, equivalents and alternatives to the various embodiments as defined by the appended claims. Moreover, with respect to the one or more methods or processes of the present disclosure described herein, including but not limited to the flow charts shown in FIG. 3 or 5, an order in which boxes or steps of the methods or processes are listed is not intended to be construed as a limitation on the claimed inventions, and any number of steps can be combined in any order and/or in parallel to implement the methods or processes described herein. Also, the drawings herein are not drawn to scale.

Conditional language, such as, among others, "can," "could," "might," or "may," unless specifically stated otherwise, or otherwise understood within the context as used, is generally intended to convey in a permissive manner that certain embodiments could include, or have the potential to include, but do not mandate or require, certain features, elements and/or boxes or steps. In a similar manner, terms such as "include," "including" and "includes are generally intended to mean "including, but not limited to." Thus, such conditional language is not generally intended to imply that features, elements and/or boxes or steps are in any way required for one or more embodiments or that one or more embodiments necessarily include logic for deciding, with or without user input or prompting, whether these features, elements and/or boxes or steps are included or are to be performed in any particular embodiment.

Although the invention has been described and illustrated with respect to exemplary embodiments thereof, the foregoing and various other additions and omissions may be made therein and thereto without departing from the spirit and scope of the present disclosure.

What is claimed is:

1. A wearable device comprising:
a glove adapted to be worn on at least a portion of a hand;
an imaging device provided on a first surface of the glove;
a first display screen provided on a second surface of the glove; and
at least one illuminator provided on the first surface of the glove,
wherein the first surface corresponds to an anterior of the glove,
wherein the second surface corresponds to a posterior of the glove,
wherein the wearable device is adapted to capture at least one image of an object within a field of view of the imaging device, and
wherein the at least one illuminator is oriented to project light onto the object within the field of view of the imaging device.

2. The wearable device of claim 1, further comprising at least one computer device configured to at least:
transmit the at least one image of the object to an external computer device over a network; and
at least one of:
cause the at least one external computer device to display the at least one image on at least one external computer display; or
cause the at least one external computer device to store the at least one image in at least one external data store.

3. The wearable device of claim 1, further comprising at least one computer device configured to at least:
cause a display of the at least one image of the object on the first display screen.

4. The wearable device of claim 1, further comprising at least one computer device configured to at least:
identify at least one marking provided on the object based at least in part on the at least one image; and identify the object based at least in part on the at least one marking.

5. The wearable device of claim 1, wherein the first display screen is at least one of:
- a liquid crystal display screen;
- a touchscreen display screen;
- an electronic ink display screen;
- a light emitting diode display screen;
- an organic light emitting diode display screen; or
- an electrophoretic display screen.

* * * * *